United States Patent [19]

Simpson

[11] Patent Number: 5,070,244

[45] Date of Patent: Dec. 3, 1991

[54] GAS DETECTION BY INFRARED ABSORPTION

[75] Inventor: Stephen W. Simpson, Blakehurst, Australia

[73] Assignee: The University of Sydney, New South Wales, Australia

[21] Appl. No.: 695,573

[22] Filed: May 3, 1991

[30] Foreign Application Priority Data

May 7, 1990 [AU] Australia .............................. PK0010

[51] Int. Cl.$^5$ ........................................... G01N 21/61
[52] U.S. Cl. ................................. 250/343; 250/351; 356/51; 356/437
[58] Field of Search .................. 250/343, 351; 356/51, 356/437

[56] References Cited

U.S. PATENT DOCUMENTS

| | | | |
|---|---|---|---|
| 4,549,080 | 10/1985 | Baskins et al. | 250/343 |
| 4,641,973 | 2/1987 | Nestler et al. | 250/351 |
| 4,772,790 | 9/1988 | Aldridge | 250/343 |

Primary Examiner—Carolyn E. Fields
Assistant Examiner—Drew A. Dunn
Attorney, Agent, or Firm—David L. Davis

[57] ABSTRACT

A method of detecting for the presence of a combustible infrared absorbing gas in air, particularly in hazardous locations such as on gas and oil rigs. A source of switched infrared radiation is beamed onto a detector within a chamber and an output signal is derived as a measure of radiation incident on the detector. A reduction in the level of the output signal indicates absorption of radiation within the chamber and, thus, indication of the presence of infrared absorbing gas within the chamber. The output signal is processed in a manner which makes provision for the existence of changing levels of background radiation which would otherwise result in a false indication of the presence or absence of combustible gas.

9 Claims, 3 Drawing Sheets

GAS DETECTION BY INFRARED ABSORPTION

FIELD OF THE INVENTION

This invention relates to a method of and apparatus for detecting the presence of a gas within an atmosphere containing the gas. The invention has particular application to the detection of a combustible gas in air and the invention is hereinafter described in such context. However, it is to be understood that the invention does have broader application, to the detection of the presence per se of any gas, for example an explosive or toxic gas, in an atmosphere containing or consisting of any other gas.

BACKGROUND OF THE INVENTION

A procedure which currently is employed for determining the presence of an explosive gas involves passing a beam of infrared radiation through a sample chamber and detecting the level of absorption of the radiation within the chamber. An output signal is derived which provides a measure of the infrared radiation which impinges on a detector, with an increase in the level of the output signal indicating a reduction in the level of infrared absorbing gas in the chamber. A filter is normally located between the radiation source and the detector to selectively pass an infrared frequency which, by its absorption, is indicative of the presence of a gas of interest.

In order to accommodate the existence of background radiation, which normally increases with increasing ambient temperature, the beam is modulated and an adjustment is made to compensate for the level of background radiation. In one known prior art system this is achieved by switching an infrared source on and off, measuring the level of radiation which is incident on the detector during an ON period, measuring the level of incident radiation during an OFF period and subtracting a signal which is representative of the second level measurement from that which is representative of the first level measurement. Any steady background infrared radiation will make the same contribution to both signals and will be cancelled when the two signals are subtracted.

A problem which is known to exist in the above described prior art system is that false readings are obtained when the background radiation level varies with time. If the background radiation changes between the OFF period and the ON period measurements of incident radiation, a false reading will be obtained when the signals that are representative of the two levels are subtracted one from the other. Given that gas detection may be required in hazardous environments, such as on oil rigs and in petrochemical plants, it is important that fast responses be obtained to indicate accurately the existence of any explosive gas mixtures and that false indications be minimized.

SUMMARY OF THE INVENTION

The present invention seeks to provide a system which makes accommodation for changes in the level of background radiation.

Broadly defined, the invention seeks to provide a method of detecting for the presence of a gas within an atmosphere and which comprises beaming infrared radiation through a chamber containing the atmosphere, modulating the radiation by cyclically switching a source of radiation on and off, detecting the level of radiation that impinges on an infrared detector within the chamber, and generating an output signal representative of the detected level. The invention is characterized in that, during predetermined periods corresponding to on-off cycles of the radiation source, the output signal from the detector is sampled and:

(a) a first signal component which is representative of the amplitude of a first extremum of the output signal is stored, (b) a second signal component which is representative of the amplitude of a second, succeeding, extremum of the output signal is stored, (c) the first signal component is subtracted from the second signal component to produce a first difference signal component, (d) the second signal component is subtracted from a third signal component which is representative of the amplitude of a third, succeeding, extremum of the output signal to produce a second difference signal component.

(e) the first difference signal is amplified by a factor which is proportional to the time period between the second and third extreme of the output signal, (f) the second difference signal is amplified by a factor which is proportional to the time period between the first and second extreme of the output signal, and (g) the two amplified difference signals are subtracted to produce an output which is representative of the level of infrared radiation attributable to the radiation source.

The first, second and third extreme result from switching of the source from one state to the other, although, depending upon the nature of the detector, the extreme need not necessarily correspond in time with switching of the source. Also, again depending upon the nature of the detector, it may be necessary to distinguish between primary extreme which reflect the source switching and secondary (less significant) extreme that may exist as a result of oscillations in the output signal.

The first extremum of the output signal may comprise a minimum signal value resulting from source switch-off prior to the commencement of an ON-OFF period. Then, the second extremum will comprise a succeeding peak signal value resulting from switching-on the source, and the third extremum will comprise a succeeding minimum signal value resulting from the next occurring source switch-off during the same ON-OFF period.

However, the first, second and third extremum may alternatively comprise peak, minimum and peak signal levels respectively during any one ON-OFF-ON sequence.

When the first extremum of the output signal comprises a minimum signal value, the first difference signal component will be amplified by a value derived as a function of $(t_{off} - t_{on})$ and the second difference signal will then be amplified by a value derived as a function of $(T - (t_{off} - t_{on}))$; where $(t_{off} - t_{on})$ is the numerical value of the time difference between the peak value of the output signal and the next succeeding minimum value in any one cycle, and where T is the numerical value of the time period of one complete cycle of the output signal.

The infrared source is preferably switched in a manner to provide an ON period which is shorter than the OFF period.

The output signal from the detector may be sampled during each succeeding ON-OFF cycle, so that a very rapid indication of the presence of an infrared-absorbing gas will be obtained. Alternatively, sampling may be effected during ON-OFF cycles that are spaced-apart in time, for example every sixty seconds.

The output resulting from subtraction of the two amplified difference signals may be employed simply to provide indication of the presence per se of infrared absorbing gas within the chamber. However, a filter may be located between the infrared source and the detector in order that selective indication may be obtained as to the composition of the absorbing gas present within the chamber. Moreover, the magnitude of the output signal may be measured to provide indication as to the proportion of infrared absorbing gas within the atmosphere containing the absorbing gas.

The invention may also be defined as providing an apparatus for detecting the presence of a gas within an atmosphere and which comprises a chamber for receiving a sample of the atmosphere, a source of infrared radiation, means for cyclically switching the source on and off, a detector for sensing the presence of incident infrared radiation and providing an output signal representative of the level of incident radiation, and circuitry for processing the output signal from the detector. The processing circuitry preferably includes two sample and hold circuits which are arranged to produce the above defined first and second difference signals and further includes means for subtracting the outputs from the two sample and hold circuits.

The invention will be more fully understood from the following description of a preferred embodiment of a gas presence detector, the description being provided with reference to the accompanying drawings.

DETAILED DESCRIPTION OF THE INVENTION

Figure 1:
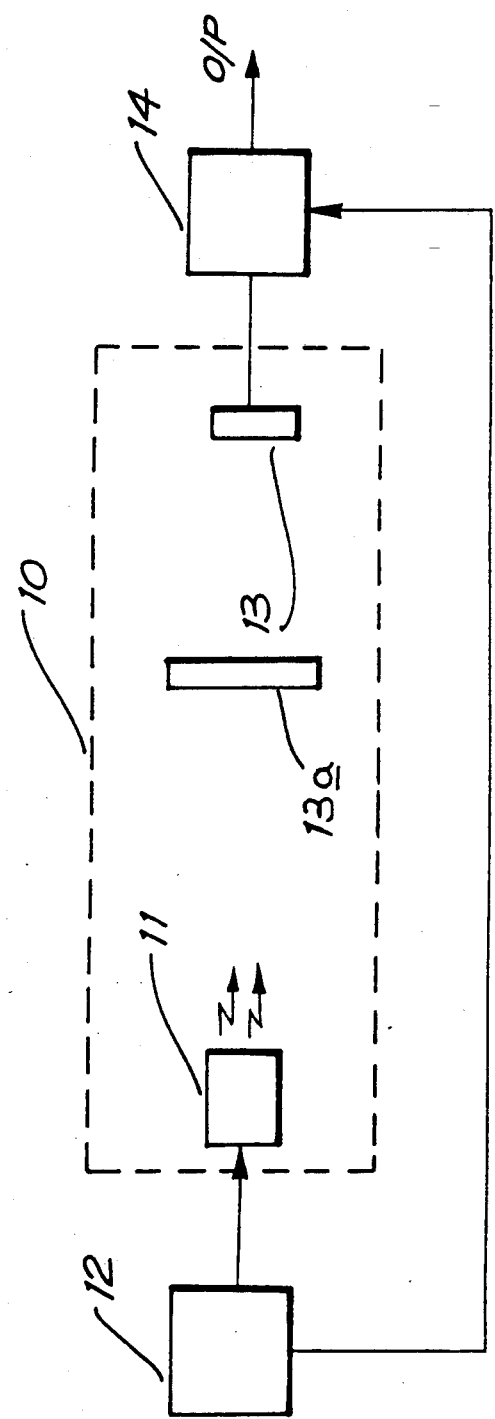
FIG. 1 shows a diagrammatic representation of the complete detector.

As illustrated, the detector comprises a chamber 10 which is constructed to admit an atmospheric gas which is to be tested or monitored for the possible inclusion of an explosive gas. An infrared generator/radiator 11 is located at one end of the chamber and is connected to associated electrical circuitry 12. The radiator may comprise a conventional incandescent lamp which is powered from a main supply, and the circuitry 12 provides for electronically controlled switching (i.e. modulation) of the lamp output. Each switched cycle of the lamp may occupy 1.5 seconds, with a 0.5 second on period followed by a 1.0 second off period. Graph 2A shows an idealized switching waveform and graph 2B shows a representative waveform of the infrared radiation envelope, this indicating the delay in build-up of the infrared level following switch-on and the delayed decay in radiation following switch-off. The mark-space ratio of the on-off switching or modulation of the infrared source may be different from that indicated (for example the ratio may be 1:1) but, due to incandescent lamps having an emissions rise time which is more rapid than the decay time, it is desirable in the interest of greater efficiency that the on time be shorter than the off time.

An infrared detector 13 is located at the opposite end of the chamber from the lamp and it provides an output signal which is representative of the level of infrared radiation which impinges on the detector. The detector 13 may comprise a simple thermopile detector, which would normally provide an output signal which follows the incident radiation waveform, or a pyroelectric detector. In the latter case the detector will produce a more complicated response to incident radiation and the time intervals of signal sampling will need to be adjusted accordingly.

A filter 13a may be located between the lamp 11 and the detector 13 and be employed to selectively pass an infrared frequency or range of frequencies which, by absorption, is indicative of the presence of a particular gas or class of gases.

The detector 13 functions to detect infrared radiation from the lamp and, also, background radiation from external sources. A steady state background will cause a dc shift in the level of the radiation from the lamp 11 and the detector output signal will then follow the waveform shown in graph 2B. Then, if the background were to remain substantially constant, relatively simple signal processing might be employed to subtract the effect of the dc shift from the detected waveform. However if, as is more likely, the background radiation changes with time, as indicated by the detector output signal waveform shown in graph 2C, known prior art forms of signal processing cannot by employed to provide an output signal which is representative of the radiation which falls incident on the detector due solely to radiation from the lamp 11.

For completeness of this description, it is mentioned that any recorded rise or fall in the level of radiation which impinges on the detector 13 (and which originates from the lamp 11) should be attributable to a reduction or increase respectively in the level of infrared absorbing gas within the chamber 10. It is important therefore that rapid compensation be made for any change in the background radiation, so that the output from the detector does provide a true indication of the presence of an absorbing gas.

Figure 3:
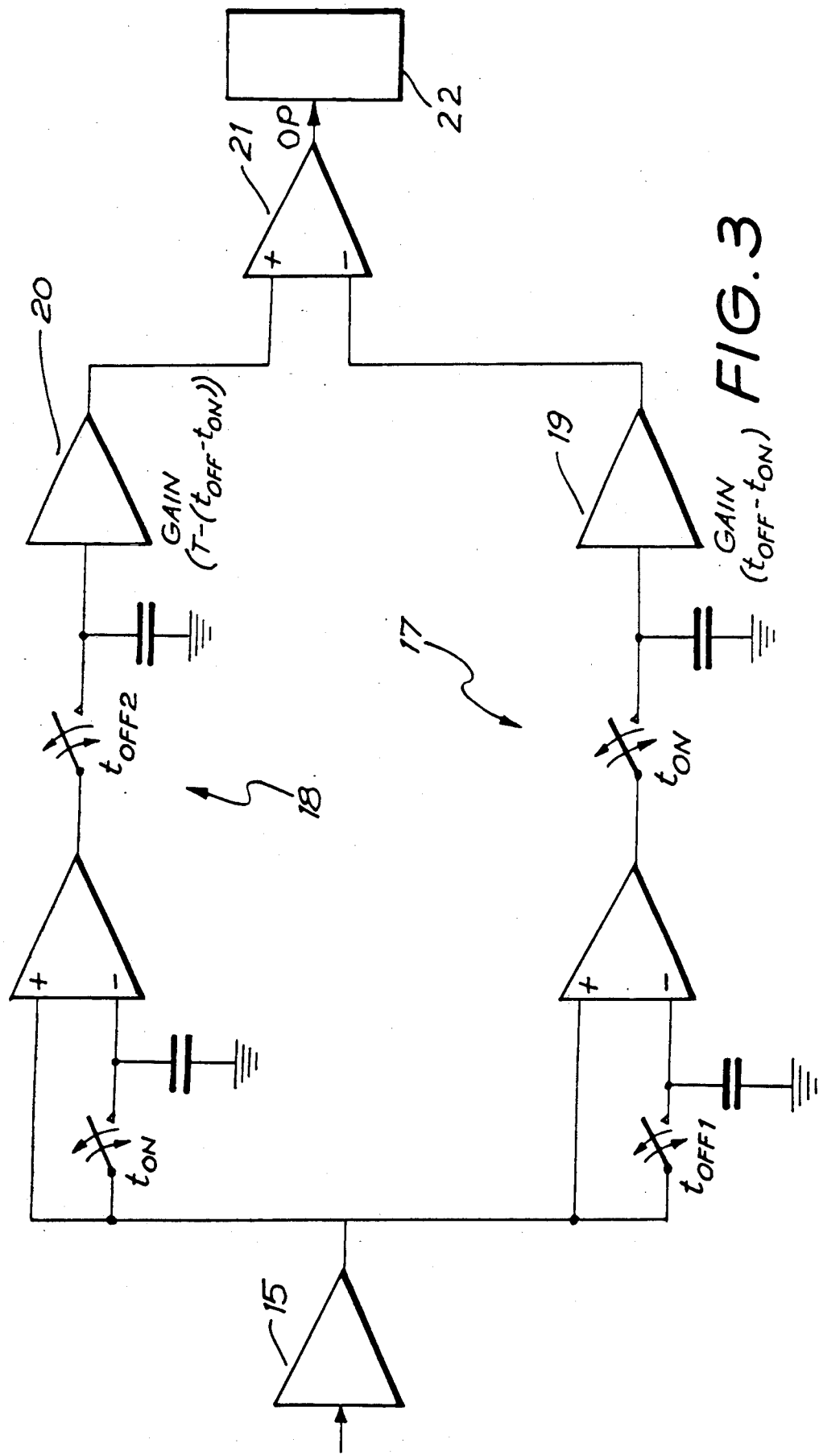
FIG. 3 shows a schematic diagram of circuitry which is employed in processing the detection signal.

A signal processing circuit 14 which is shown in greater detail in FIG. 3 is employed to accommodate background radiation which changes with time but, before proceeding to a description of the circuitry, it is appropriate to provide a brief description of the mathematical operations which are performed by the circuitry.

Figure 2:
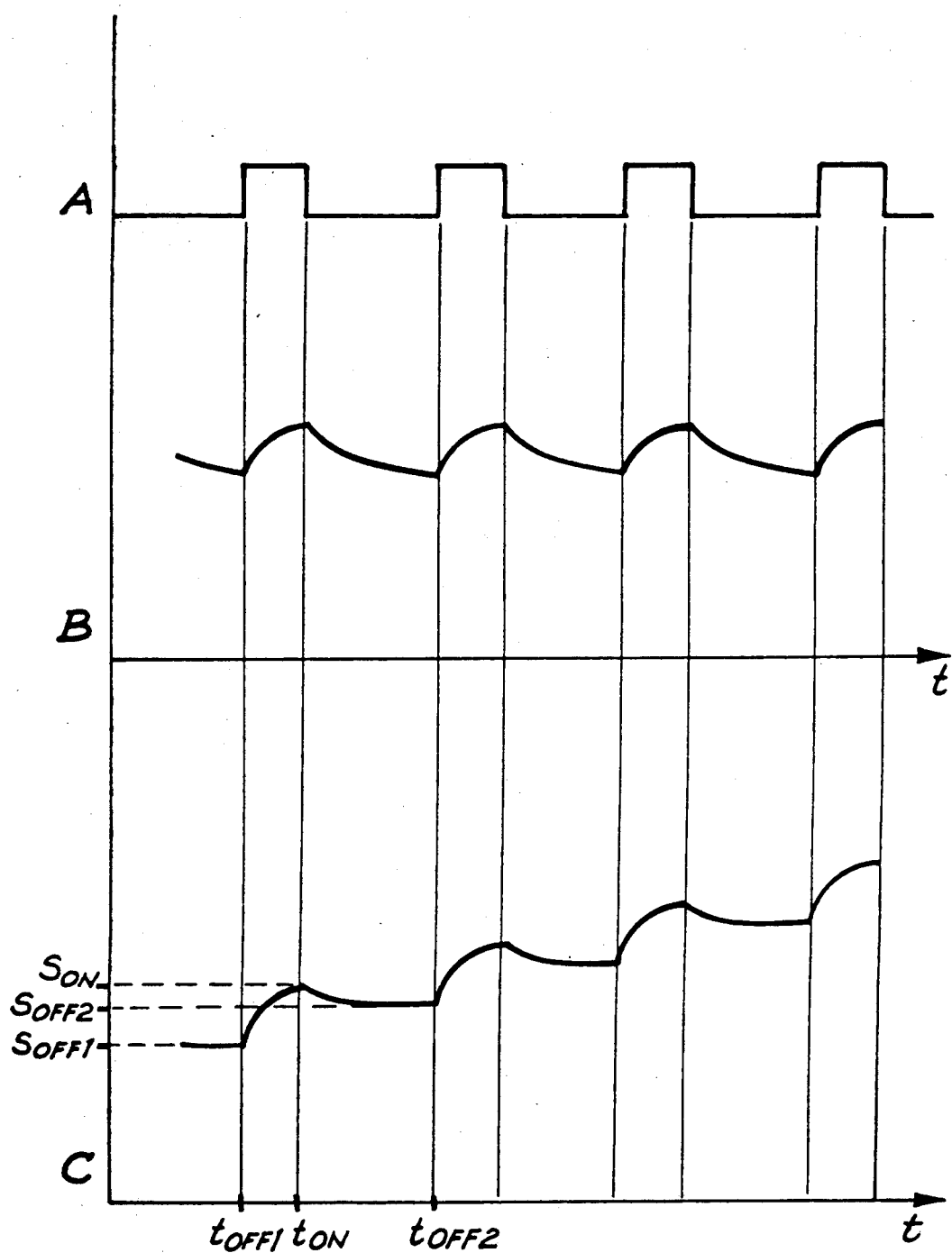
FIG. 2 shows a series of graphs which are representative of infrared radiation and detection signals.

In referring to graph C in FIG. 2, a measure of the peak extremum $S_{on}$ of the detector output signal is derived at time $t_{on}$, this resulting from excitation of the lamp Also, a measure of the minimum extremum $S_{off1}$ of the detector output signal is derived at the earlier time $t_{off1}$, and a measure of a (different level) minimum extremum $S_{off2}$ is derived at the later time instant $t_{off2}$. The shape of the detector output signal will depend both on the source 11 and on the type of detector 13 that is used. For some types of detectors, for example pyroelectric detectors, the peak and minimum values in the output waveform will not necessarily coincide in time with the switching of the source, and it is j to be understood that the time instant $t_{on}$ etc may apply only to the detector output waveform and not to the switching intervals of the lamp 11.

Employing the above terms, the level of radiation incident on the detector can be expressed mathematically as being proportional to:

$$(t_{off2}-t_{on})S_{off1}-TS_{on}+(T-(t_{off2}-t_{on}))S_{off2}.$$

Thus, a signal which is proportional to this expression is produced by the detector 13 for each lamp switching cycle, where T is the duration $(t_{off2}-t_{off1})$ of one complete cycle.

The above expression can be rewritten as:

$$(T-(t_{off2}-t_{on}))O_2-(t_{off2}-t_{on})O_1$$

where the term $O_2$ corresponds with $(S_{off2}-S_{on})$ and the term $O_1$ corresponds with $(S_{on}-S_{off})$.

This expression is used for controlling the processing circuitry which is shown in FIG. 3.

As shown in FIG. 3, the output signal from the detector 13 is fed to an input amplifier and filter 15. Also, although not shown, the input circuit may include provision for static temperature compensation, with provision thus being made for changing the gain in the amplifier 15 as a function of temperature.

The conditioned detector output signal is then applied to two sample and hold circuits 17 and 18. In respect of each complete cycle of the detector output signal, the first sample and hold circuit 17 stores the minimum value $S_{off1}$ of the signal at time $t_{off1}$ and subtracts it from the following peak value $S_{on}$ of the signal at time $t_{on}$. The second circuit 18 stores the peak value $S_{on}$ of the signal, also at time $t_{on}$, and then subtracts it from the following minimum signal value $S_{off2}$ at time $t_{off2}$.

Amplifiers 19 and 20 in the respective sample and hold circuits 17 and 18 increase the amplitude of the difference signals which are derived from the respective sample and hold circuits. Amplifier 19 is set to provide a gain corresponding numerically (i.e. proportionately) to the time period $(t_{off2}-t_{on})$, and the amplifier 20 has its gain set to a numerical value corresponding to a time period $T-(t_{off2}-t_{on})$.

The outputs from the two sample and hold circuit 17 and 18 are then applied to a following subtractor/filter circuit 21 where the signal corresponding to the expression $(t_{off2}-t_{on})(S_{on}-S_{off1})$ is subtracted from the signal corresponding to the expression $(T-(t_{off2}-t_{on}))(S_{off2}-S_{on})$.

As hereinbefore mentioned, this signal provides a measure of the infrared radiation incident on the detector 13 due solely to radiation emitted by the lamp 11. Thus, the output signal from the subtracting circuit 21 is representative of the amount of infrared absorbing gas within the chamber 10.

The output from the subtractor circuit 21 is applied as an input signal to a following alarm or metering apparatus 22 which, depending on the requirements of the system, may provide indication of the presence, level or composition of infrared absorbing gas within the chamber 10.

I claim:

1. A method of detecting for the presence of a gas within an atmosphere and which comprises beaming infrared radiation through a chamber containing the atmosphere, modulating the radiation by cyclically switching a source of the radiation on and off, detecting the level of radiation that impinges on an infrared detector within the chamber and generating an output signal representative of the detected level; characterized in that, during predetermined periods corresponding to on-off cycles of the radiation source, the output signal from the detector is sampled and:
   (a) a first signal component which is representative of the amplitude of a first extremum of the output signal is stored,
   (b) a second signal component which is representative of the amplitude of a second, succeeding, extremum of the output signal is stored,
   (c) the first signal component is subtracted from the second signal component to produce a first difference signal,
   (d) the second signal component is subtracted from a third signal component which is representative of the amplitude of a third, succeeding, extremum of the output signal to produce a second difference signal,
   (e) the first difference signal is amplified by a factor which is proportional to the time period between the second and third extreme of the output signal,
   (f) the second difference signal is amplified by a factor which is proportional to the time period between the first and second extreme of the output signal, and
   (g) the two amplified difference signals are subtracted to produce an output which is representative of the level of infrared radiation attributable to the radiation source.

2. The method as claimed in claim 1 wherein the output signal is sampled during each of the periods that correspond to the on-off cycles of the radiation source.

3. The method as claimed in claim 1 wherein the source of radiation is switched on for a period which is shorter than the off period.

4. The method as claimed in claim 1 wherein the output which is representative of the level of infrared radiation directed to means for indicating the presence of the gas within the atmosphere.

5. The method as claimed in claim 1 wherein the output which is representative of the level of infrared radiation is directed to means for determining the proportion of infrared absorbing gas within the gas contained by the chamber.

6. The method as claimed in claim wherein the radiation from the source is directed to the detector by way of a filter which is selected to pass a band of infrared frequencies which is characteristically absorbed by a gas whose presence is to be detected.

7. The method as claimed in claim 1 wherein the first signal component is representative of the amplitude of a first minimum value of the output signal in a predetermined period, the second signal component is representative of the amplitude of a succeeding maximum value of the output signal in the predetermined period and the third signal component is representative of the amplitude of a succeeding second minimum value of the output signal in the predetermined period.

8. The method as claimed in claim 1 wherein the first signal component is representative of the amplitude of a first peak value of the output signal in a predetermined period, the second signal component is representative of the amplitude of a succeeding minimum value of the output signal in the predetermined period and the third signal component is representative of the amplitude of a second peak value of the output signal in the predetermined period 9. An apparatus for detecting the presence of a gas within an atmosphere and which comprises a chamber for receiving a sample of the atmosphere, a source of infrared radiation, means for cyclically switching the source on and off, a detector for sensing the presence of incident infrared radiation and providing an output signal representative of the level of incident radiation, and processing circuitry for processing the output signal from the detector; characterized in that the processing circuitry includes means for sampling and deriving first, second and third signal components which are representative of the amplitude of first, second and third extrema respectively in predetermined periods corresponding to on-off cycles of the radiation source, means for subtracting the first signal component from the second signal component to produce a first difference signal, means for subtracting the second signal component from the third signal component to produce a second difference signal, means for amplifying the first difference signal by a factor which is proportional to the time period between the second and third extrema in the output signal, means for amplifying the second difference signal by a factor which is proportional to the time period between the first and second extrema of the output signal, and means for subtracting the two amplified difference signals to produce an output which is representative of the level of infrared radiation attributable to the radiation source.

* * * * *